United States Patent [19]

Mosse et al.

[11] Patent Number: 4,720,581
[45] Date of Patent: Jan. 19, 1988

[54] BENZAMIDINE DERIVATIVES

[75] Inventors: Madeleine Mosse; Henri Demarne; Robert Filhoi, all of Montpellier, France

[73] Assignee: Sanofi, France

[21] Appl. No.: 631,753

[22] Filed: Jul. 17, 1984

[30] Foreign Application Priority Data

Aug. 3, 1983 [FR] France .................. 83 12824

[51] Int. Cl.$^4$ .......................................... C07C 123/00
[52] U.S. Cl. ................................................ 564/247
[58] Field of Search ............... 564/247; 424/326, 64, 424/69, 70, 358; 426/331, 333; 514/637; 422/28

[56] References Cited

U.S. PATENT DOCUMENTS 2,934,438  4/1960  Michener et al. ................ 426/331
3,769,427  10/1973  Hughes et al. .................... 424/358

FOREIGN PATENT DOCUMENTS 139921  1/1951  Australia ........................... 564/247

OTHER PUBLICATIONS

Kirk–Othmer Encyclopedia of Chemical Technology, 2nd Ed., vol. 2, pp. 604–615.
Wagner, G et al., *Chemical Abstracts*, vol. 84 (1976), #43, 563n.
Pharmazie, vol. 30, No. 6, Jun. 1975, pp. 386–389, Berlin (DE); P. Walsmann et al.: "Synthetische Inhibitoren der Serinproteinasen". *p. 387: Tableau 2*.

*Primary Examiner*—Donald B. Moyer
*Assistant Examiner*—L. Hendriksen
*Attorney, Agent, or Firm*—Bacon & Thomas

[57] ABSTRACT

The present invention relates to benzamidine derivatives corresponding to the general formula

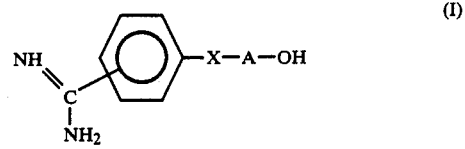

in which:
A represents a linear or branched alkyl chain containing from 3 to 9 carbon atoms; and
X represents the oxygen atom or a direct bond, with the restriction that if X represents a direct bond, the benzamidine and the alkanol group are located in the para position, and also the pharmaceutically acceptable salts of the products of the formula (I);

it also relates to a process for the preparation of the products of the formula (I) and the drugs for external use which contain a product of the formula (I).

6 Claims, No Drawings

BENZAMIDINE DERIVATIVES

The present invention relates to new benzamidine derivatives corresponding to the following general formula:

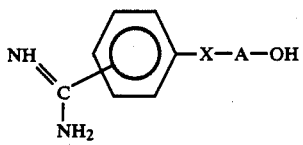
(I)

in which:
- A represents a linear or branched alkyl chain containing from 3 to 9 carbon atoms; and
- X represents the oxygen atom or a direct bond.

If X represents a direct bond, the benzamidine is located in the para position relative to the alkanol group.

The present invention also comprises the pharmaceutically acceptable salts of the compounds (I).

These compounds have an antimicrobial activity and they can be used, in particular, as antiseptic drugs for human or veterinary purposes or as disinfectants on inert surfaces. They can also be used as preservatives.

The compounds according to the invention are prepared from the nitrophenylalkanols or nitrophenoxyalkanols (IV). Catalytic hydrogenation gives the corresponding aniline derivatives (V) and the addition of sodium nitrite in an acid medium then gives the diazonium compounds. The action of cuprous cyanide subsequently leads to the benzonitrile derivatives (VI) by the Sandmeyer reaction. Finally, the amidines (I) are synthesized by a reaction known per se, which comprises the intermediate formation of an iminoester.

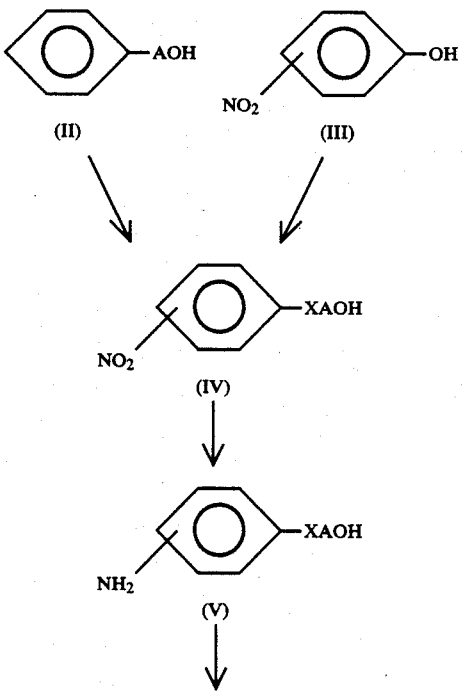

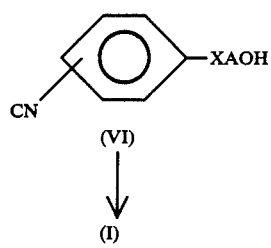

If X represents a direct bond, the nitrophenylalkanol (IV) is prepared from the phenylalkanol (II). The hydroxyl group is protected beforehand by acetylation using acetyl chloride. After nitration with fuming nitric acid, the alcohol is freed by reaction with a solution of hydrogen chloride in methanol.

The phenylalkanols (II) are commercially available where linear alcohols are concerned. Otherwise, they can be prepared by a variety of methods. For example, the secondary phenyl alcohols are prepared from phenylacetaldehyde by reaction with a magnesium derivative followed by hydrolysis:

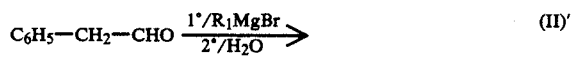

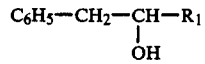

$R_1$: alkyl having 1 to 8 carbons.

The primary branched phenylalkanols are obtained from benzyl cyanide:

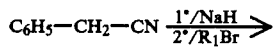

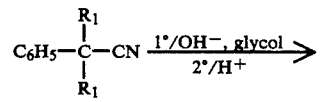

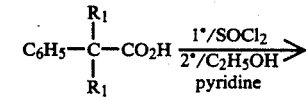

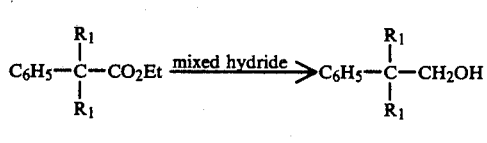

After reaction with sodium hydride in an anhydrous medium, it is possible to add an alkyl halide, for example an alkyl bromide, to give a symmetrical dialkylated phenylacetonitrile. This compound is converted to the acid by reaction with a base in an alcoholic medium, followed by acidification.

Reaction with thionyl chloride and then with ethyl alcohol in an anhydrous medium, in the presence of a catalyst, for example pyridine or dimethylaminopyridine, makes it possible to obtain the ethyl ester (VIII). The corresponding alcohol (II)" is then prepared by reduction with a mixed anhydride in an anhydrous solvent.

If X represents oxygen, the nitrophenoxyalkanol (IV) is prepared from nitrophenol (III). Reaction of an alkyl dihalide with (III) in a basic medium makes it possible to obtain a nitrophenoxyalkyl halide (IX). This product is acetylated in an acid medium and (IV) is then freed by saponification.

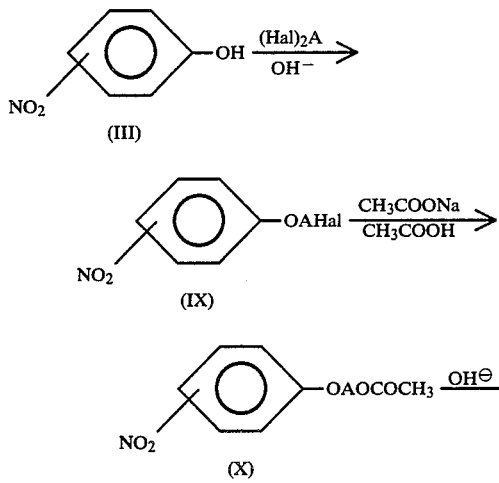

The examples which follow illustrate the invention without however restricting it. If the product obtained is in the form of an oil, it is characterized by its nuclear magnetic resonance (NMR) spectrum. This is recorded at 60 MHz in deuterochloroform, hexamethyldisiloxane being taken as the internal standard.

The following abbreviations are used to describe the spectrum:
S: singlet
D: doublet
T: triplet
Q: quadruplet
M: multiplet
J: coupling constant.

EXAMPLE 1

4-(3-Hydroxypropyl)benzamidine hydrochloride: SR 41326 A (a)—3-(4-Nitrophenyl)propan-1-ol.

95 ml of acetyl chloride are added to 171.5 g of 3-phenylpropan-1-ol over a period of one hour, with stirring. The mixture is heated under reflux for 2 hours and the hydrogen chloride evolved and the excess acetyl chloride are removed. When the reaction medium has returned to ambient temperature, it is poured dropwise, with stirring, into 800 ml of fuming nitric acid (d=1.49) cooled to −25° C.; the addition takes 1 hour, during which time the temperature is kept at between −15° C. and −20° C. The mixture is subsequently poured into 1.5 liters of water to which crushed ice has been added, extraction is then carried out 3 times with ether and the extracts are washed 3 times with water, 3 times with a 10% solution of sodium carbonate and then 3 times with water. The ether phases are dried over magnesium sulfate and then evaporated to dryness under reduced pressure. The residue is taken up in 800 ml of methanol, hydrogen chloride is then bubbled through for 1 hour at 0° C. and the mixture is subsequently heated under reflux for 14 hours. After evaporation of the solvent, the residue is taken up in a water/ether mixture, the aqueous phase is decanted and the organic phase is washed twice with water, 3 times with a saturated solution of sodium bicarbonate and then 3 times with water; the ether phase is subsequently dried over magnesium sulfate and then evaporated to dryness under reduced pressure.

This gives 259 g of an orange oil which is purified by chromatography on 3 kg of silica gel in chloroform; 218 g of an orange oil are recovered; yield: 95%.

(b)—4-(3-Hydroxypropyl)aniline.

218 g of 3-(4-nitrophenyl)propan-1-ol are dissolved in 500 ml of methanol, and 10 g of 10% palladium-on-charcoal, moistened beforehand with 10 ml of water, are added. Hydrogenation is carried out under a pressure of 40 bar, with stirring, and takes 1 hour 30 minutes. The mixture is then filtered on cellite, the material on the filter is rinsed with methanol and the filtrate is evaporated to dryness under reduced pressure to give 168 g of a brown oil. This is purified by chromatography 3 times in succession on a total of 6 kg of alumina, methylene chloride being used as the eluent. This gives 49.2 g of a light brown powder; m.p. (c)=43°–45° C.; yield: 27%.

(c)—4-(3-Hydroxypropyl)benzonitrile.

49.07 g of the previously obtained product are poured into 87 ml of concentrated hydrochloric acid to which 400 g of crushed ice have been added. With the temperature kept at between 0° C. and 5° C., a solution of 23.15 g of sodium nitrite in 80 ml of water is added dropwise and then, after stirring for 10 minutes, the mixture is neutralized with 300 ml of a 10% solution of sodium carbonate.

A solution of cuprous cyanide is prepared separately: 40.35 g of cuprous chloride are suspended in 150 ml of water, and a solution of 54 g of sodium cyanide in 80 ml of water is added. The evolution of heat is observed, the cuprous chloride dissolves and the solution is decolorized. This solution is cooled to 0° C. and 200 ml of benzene are added, after which the diazonium solution, cooled to 0° C., is added dropwise over a period of 40 minutes, with vigorous stirring. After stirring for a further 40 minutes, the mixture is allowed to return to ambient temperature, with continued stirring, and then heated to 50° C., without stirring, and brought back to ambient temperature.

Extraction is carried out 3 times with ether and the extracts are washed twice with water and then with a saturated solution of sodium chloride. The ether phases are dried over magnesium sulfate and evaporated to dryness under reduced pressure. This gives 51 g of a dark brown oil which is purified by chromatography on 1500 g of silica gel, the column being prepared in toluene and the eluent being a toluene/ether mixture (9/1 by volume). This gives 41.6 g of a pure product in the form of a red oil; yield: 79%.

The product is characterized by its NMR spectrum: 2H at between 1.7 and 2.2 ppm (M, —CH$_2$—CH$_2$—CH$_2$—OH); 1H at 2.4 ppm (S, —OH); 2H at 2.8 ppm (T, J=7 Hz, CN—C$_6$H$_4$—CH$_2$—CH$_2$—); 2H at 3.6 ppm (T, J=6 Hz, —CH$_2$—CH$_2$—OH); 2H at 7.3 ppm (D, J=9 Hz, H ortho to CH$_2$); 2H at 7.6 ppm (D, J=9 Hz, H ortho to CN).

(d)—Ethyl 4-(3-hydroxypropyl)phenylformimidate hydrochloride.

30.6 g of the previously obtained product are dissolved in 300 ml of absolute alcohol, hydrogen chloride is bubbled through at 0° C. for 5 hours, the mixture is then left to stand for 24 hours at ambient temperature, the solvents are evaporated off to dryness under reduced pressure and the residue is precipitated in 1 liter of ether. The mixture is stirred for 1 hour at 0° C. and then filtered and the material on the filter is washed with ether and dried in a vacuum desiccator over phosphorus pentoxide. This gives 40 g of a pink powder; m.p. (k)=104°-105° C. with decomposition; yield: 86%.

(e)—SR 41326 A.

40 g of the previously obtained product are dissolved in 400 ml of absolute alcohol. Ammonia gas is bubbled through at 0° C. for 5 hours and the mixture is then stirred at ambient temperature and left to stand for 48 hours. The solvents are then evaporated off to dryness under reduced pressure and the residue is taken up in 500 ml of distilled water. The mixture is stirred for 1 hour with 450 ml of Amberlite IRA 400 resin in the acetate form, and then filtered, and the material on the filter is washed 3 times with 300 ml of water. The filtrates are subsequently stirred with 400 ml of Bio-Rex 70 resin in the acidic form, and then filtered, and the material on the filter is washed 3 times with 500 ml of water.

The amidine is eluted from the resin with 500 ml portions of 5% aqueous hydrochloric acid. The solvent is then evaporated off under reduced pressure to give yellow crystals, these are taken up in alcohol and the alcohol is then evaporated off (repeated 3 times). The residue is taken up in 1 liter of ether and triurated in the cold to give a yellow powder which is filtered off, washed with ether and dried in a vacuum desiccator over phosphorus pentoxide. This gives 20.1 g of the expected product in the form of a light yellow powder; m.p. (c)=195°-205° C.; yield: 57%.

EXAMPLE 2

4-(2-Hydroxybutyl)benzamidine hydrochloride: CM 41092 A (a)—1-Phenylbutan-2-ol.

A solution of 7.5 ml of ethyl bromide in 50 ml of anhydrous ether is added dropwise, under nitrogen, to 2.92 g of magnesium turnings at a sufficient rate to maintain gentle reflux. Still under nitrogen, the mixture is stirred for 2 hours at ambient temperature, 9.4 ml of phenylacetaldehyde are then added dropwise and the mixture is stirred for 2 hours at ambient temperature.

The mixture is then poured into 200 ml of 20% ammonium chloride solution cooled to 0° C., and extraction is carried out 3 times with ether. After the ether phases have been washed 3 times with water, they are dried over magnesium sulfate and evaporated to dryness under reduced pressure. This gives 12.2 g of a slightly yellow oil.

(b)—4-(2-Hydroxybutyl)benzonitrile.

By following the procedure of Example 1(a), 1-(4-nitrophenyl)butan-2-ol is then prepared, which is characterized by its NMR spectrum: 3H at 0.9 ppm (asymmetrical T, J=7 Hz, —CH$_3$); 3H at between 1.2 and 1.8 ppm (unresolved peaks, —CH(OH)—CH$_2$—CH$_3$); 2H at between 2.6 and 2.9 ppm (M, CN—C$_6$H$_4$—CH$_2$); 1H at between 3.4 and 3.9 ppm (M, CH$_2$—CH(OH)—CH$_2$); 2H at 7.3 ppm (D, J=9 Hz, H ortho to CH$_2$); 2H at 8.1 ppm (D, J=9 Hz, H ortho to CN).

4-(2-Hydroxybutyl)benzonitrile is then prepared as in Example 1 (b) and (c) and is also characterized by its NMR spectrum: 3H at 0.8 ppm (asymmetrical T, J=6 Hz, —CH$_2$—CH$_3$); 2H at 1.25 (Q, J=6 Hz, —CH(OH)—CH$_2$—CH$_3$); 2H at between 2.5 and 2.8 ppm (M, CN—C$_6$H$_4$—CH$_2$); 1H at between 3.2 and 3.8 ppm (M, CH$_2$—CH(OH)—CH$_2$); 1H at 4.5 ppm (D, J=6 Hz, —OH); 2H at 7.4 ppm (D, J=9 Hz, H ortho to CH$_2$); 2H at 7.7 ppm (D, J=9 Hz, H ortho to CN).

(c)—Ethyl 4-(2-hydroxybutyl)phenylformimidate hydrochloride.

This product is prepared by the procedure described in Example 1 (d) and recrystallized from an ethanol/ether mixture; m.p. (c)=118°-122° C. with decomposition.

(d)—CM 41092 A.

The expected product is prepared according to Example 1 (e); m.p. (c)=159°-161° C.; recrystallization solvent: ethanol/ether.

EXAMPLE 3

4-(2-Hydroxy-1,1-di-n-propylethyl)benzamidine hydrochloride: SR 41946 A (a)—1,1-Di-n-propylphenylacetonitrile.

A suspension of 52.4 g of sodium hydride in 250 ml of dimethylformamide is prepared. Under nitrogen and with constant mechanical stirring, 47 ml of benzyl cyanide are added, after 35 minutes the mixture is cooled in an ice bath and 145 ml of n-propyl bromide are then added very slowly. Stirring is then continued for 3 hours at ambient temperature.

The mixture is poured into 2 liters of water mixed with ice, extraction is then carried out twice with ether and the ether phases are washed 3 times with water and dried over magnesium sulfate. After evaporation of the ether, the residue is distilled in vacuo; b.p.=72°-80° C. under 0.01 mm Hg. This gives 50.4 g of a yellow oil; yield: 63%.

(b)—1,1-Di-n-propylphenylacetic acid.

25.1 g of the previously obtained product are dissolved in 65 ml of glycol, and 15.5 g of potassium hydroxide pellets are added. By heating, with stirring, 2 ml of water are initially distilled, heating is then continued under reflux for 40 hours, with stirring, and 1.5 liters of water to which ice has been added are poured in. Extraction is carried out twice with hexane, the aqueous phase is filtered on cellite and the filtrate is acidified to pH 1 with concentrated hydrochloric acid. The white precipitate formed is left to stand in a refrigerator for 48 hours, filtered off, washed with water and recrystallized from a methanol/water mixture (50/50 by volume). The crystals formed are filtered off, washed with water and dried in vacuo.

This gives 18.75 g of grayish-white crystals; m.p. (c)=97°-100° C.; yield: 68%.

(c)—Ethyl 1,1-di-n-propylphenylacetate.

The following reaction is carried out under nitrogen. 10 ml of thionyl chloride are added dropwise to 8.8 g of the previous product, with stirring. Stirring is continued for 2 hours at ambient temperature, the mixture is then cooled and the excess thionyl chloride is driven off under reduced pressure. 50 ml of absolute alcohol and 3.5 ml of anhydrous pyridine are then added at 0° C., after stirring for 1 hour the mixture is heated under reflux for 15 hours and then cooled, the alcohol is evaporated off and the residue is taken up in a water/ether mixture, extraction is carried out 3 times with ether and the extracts are washed twice with a saturated solution of sodium bicarbonate, once with water, twice with normal hydrochloric acid and then 3 times with water. The ether phases are then dried over magnesium sulfate and evaporated to dryness under reduced pressure.

This gives 9.82 g of an orange oil; yield: 99%. The product is characterized by its NMR spectrum: 13H at between 0.6 and 1.4 ppm (unresolved peaks, —CO$_2$—CH$_2$—CH$_3$, (—CH$_2$—CH$_2$—CH$_3$)$_2$); 4H at between 0.8 and 2.2 ppm (unresolved peaks, (—CH$_2$—CH$_2$—CH$_3$)$_2$); 2H at 4.1 ppm (Q, J=7 Hz, —CO$_2$—CH$_2$—CH$_3$); 5H at 7.3 ppm (S, aromatic H).

(d)—1,1-Di-n-propylphenylethanol.

3.2 g of lithium aluminum hydride are suspended in 50 ml of anhydrous tetrahydrofuran under nitrogen. A solution of 9.8 g of the product obtained under (c) in 50 ml of tetrahydrofuran is added dropwise while maintaining gentle reflux, and the mixture is then heated under reflux for 4 hours, still under nitrogen. After cooling, the product is decomposed with 10 ml of water and 100 ml of 15% sulfuric acid. Extraction is carried out 3 times with ether and the ether phases are washed 3 times with water, dried over magnesium sulfate and evaporated to dryness under reduced pressure.

This gives 8.30 g of a yellow oil which is purified by chromatography on 250 g of silica gel, a chloroform/hexane mixture (50/50 by volume) being used as the eluent. 7.91 g of a slightly yellow oil are thus collected; yield: 97%.

The product is characterized by its NMR spectrum: 15H at between 0.5 and 1.8 ppm (unresolved peaks, 14H of the aliphatic chains+OH); 2H at 3.7 ppm (S, —CH$_2$—OH); 5H at 7.25 ppm (S, aromatic H).

(e)-SR 41946 A.

The synthesis steps described in Example 1 are then carried out in order to prepare SR 41946 A; m.p. (c)=110°–115° C.; recrystallization solvent: ethanol/ether mixture.

EXAMPLE 4

4-(4-Hydroxybutoxy)benzamidine: CM 40847 A (a)—1-(4-Nitrophenoxy)-4-bromobutane.

83 ml of 1,4-dibromobutane are added to a solution of 4-nitrophenol in 275 ml of water, and 49.5 ml of 10N sodium hydroxide solution are then added dropwise, with stirring. The mixture is heated under reflux for 24 hours, with stirring.

After cooling, extraction is carried out 3 times with ether and the extracts are washed 6 times with normal sodium hydroxide solution and then 3 times with water. The ether phases are dried over sodium sulfate and evaporated and the insoluble material is filtered off. The filtrate is evaporated to dryness and the residue is pumped in vacuo (0.05 mm Hg). After trituration in hexane, crystals are obtained which are filtered off, washed with hexane and dried in a vacuum desiccator.

This gives 75 g of a pasty cream-colored product; yield: 55%.

(b)—1-(4-Nitrophenoxy)-4-acetyloxybutane.

75 g of the previous product are dissolved in 80 ml of glacial acetic acid, 45 g of anhydrous sodium acetate are added and the mixture is then heated under reflux for 15 hours, with stirring. The reaction mixture is poured into one liter of iced water to which 500 ml of ether have been added, and neutralized to pH 7.5 with solid sodium carbonate. After 3 extractions have been carried out with ether and the extracts washed 3 times with water, the ether phases are dried over magnesium sulfate and evaporated to dryness and the residue is pumped in vacuo.

This gives 70 g of an orange oil; yield: 100%.

(c)—1-(4-Nitrophenoxy)butan-4-ol.

70 g of the previously obtained product are dissolved in 300 ml of methanol, 30 ml of 10N sodium hydroxide solution are added and the mixture is then heated under reflux for 4 hours, with stirring. After the methanol has been evaporated off, the residue is taken up in a water/ether mixture, extraction is carried out 3 times with ether and the extracts are washed 3 times with a saturated solution of sodium chloride.

The ether phases are then dried over magnesium sulfate and evaporated to dryness. The crystals formed are triturated in hexane, filtered off, washed with hexane and dried in a vacuum desiccator.

This gives 48.8 g of slightly yellow crystals; m.p. (c)=53°–55° C.

(d)—CM 40847.

The following compounds are then prepared by the procedure of Example 1:

4-(4-hydroxybutoxy)aniline.
   m.p. (c)=56°–58° C.
4-(4-hydroxybutoxy)benzonitrile.
   m.p. (c)=54°–58° C.
then CM 40847 A.
   m.p. (c)=210°–213° C.

The compounds according to the invention which are described in Table 1 below are prepared using analogous processes of preparation. They are characterized by the melting point of the hydrochloride, measured after recrystallization from an ethanol/ether mixture.

TABLE 1

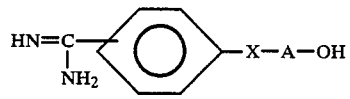

(I)

| Product No. | Position | X | A—OH | Prepared according to Example | Melting point |
|---|---|---|---|---|---|
| SR 41613 A | p | — | (CH$_2$)$_4$OH | 1 | 178–180° C. |
| SR 41947 A | p | — | (CH$_2$)$_5$OH | 1 | 210–215° C. |
| SR 41149 A | p | — | CH$_2$—CH(OH)nC$_3$H$_7$ | 2 | 85–90° C. |
| CM 40721 A | p | 0 | —(CH$_2$)$_3$OH | 4 | 161–163° C. |
| CM 40940 A | p | 0 | —(CH$_2$)$_5$OH | 4 | 180–185° C. |
| SR 41579 A | m | 0 | —(CH$_2$)$_4$OH | 4 | 141–143° C. |
| SR 41616 A | o | 0 | —(CH$_2$)$_4$OH | 4 | 152–154° C. |
| SR 42748 A | p | — | —C(CH$_3$)$_2$CH$_2$OH | 3 | 181° C. |

The bactericidal activity of the products according to the invention was studied on different strains by the method described below:

A bacterial inoculum is brought into contact for a limited time with different dilutions of the product to be tested. At the end of the contact period, an aliquot of the mixture of bacterial suspension and product is deposited on the surface of a gelose culture medium containing a neutralizer of the antibacterial activity of the product.

The bactericidal concentration selected is the minimum concentration of product beyond which the bacteria no longer grow. This concentration is expressed in μg/ml.

The bacterial strains chosen for the study are:

1—*Escherichia coli* CNCM 54125;
2—Capsular *Klebsiella pneumoniae* R030;
3—*Pseudomonas aeruginosa* CNCM A22;
4—*Streptococcus faecalis* CNCM 5855;
5—*Staphylococcus aureus* CNCM 53154.

The second strain is kept on a Worgel Fergusson medium and the others on Tryptic Soy Agar-Difco (TSA).

After 24 hours of culture at 37° C., the microbial growth is harvested using glass beads and 10 ml of a diluent containing 1 g of tryptone and 8.5 g of sodium chloride in 1000 ml of distilled water. The suspension formed is stirred and the percentage transmission of light at 620 nm is measured with a spectrophotometer:

Strain 1: 70%;
Strain 2: 80%;
Strain 3: 70%;
Strain 4: 60%;
Strain 5: 60%.

The bacterial inoculum corresponds to a suspension whose concentration is 1/20th that of this bacterial suspension.

Plates containing cups receive different dilutions of the product to be studied. These dilutions of the product to be studied are brought into contact with the different bacterial suspensions using a Steers-type multiple site inoculator. After a contact time of 20 minutes, aliquots are transferred with this inoculator to the surface of a gelose medium (TSA) placed in Petri dishes, containing an activity neutralizer, namely 20 g of lubrol W, 2.5 g of Tween 80 and 2.5 g of sodium thiosulfate in 1000 ml of TSA (Difco). A control for the efficacy of the neutralizer is prepared for each product studied by depositing, on the surface of the culture medium, an aliquot of the dilution of the product to be studied. After drying, the corresponding inoculum is deposited in the same place. An inoculum control is prepared on gelose medium with and without neutralizer. The results are assessed after incubation for 48 hours at 37° C.

The results are collated in Table 2 below.

TABLE 2

| | Minimum bactericidal concentration (MBC) in µg/ml | | | | |
|---|---|---|---|---|---|
| | Bacterial strains | | | | |
| Product No. | 1 | 2 | 3 | 4 | 5 |
| SR 41613 A | 10000 | 10000 | 15000 | 10000 | 5000 |
| SR 41946 A | 4000 | 5000 | 4000 | 2000 | 2000 |
| SR 42748 A | 10000 | 10000 | ≦5000 | 20000 | 10000 |
| SR 41149 A | 5000 | 6000 | 6000 | 20000 | 20000 |
| CM 40721 A | 8000 | 8000 | 8000 | 8000 | 8000 |
| CM 40847 A | 5000 | 5000 | 5000 | 5000 | 5000 |
| SR 41616 A | 7500 | 5000 | 5000 | 15000 | 15000 |
| CM 40940 A | 16000 | 15000 | 15000 | 20000 | 15000 |
| SR 41579 A | 8000 | 8000 | 8000 | 10000 | 15000 |

The results show that the products according to the invention have a comparable level of activity over the whole range of bacterial strains tested.

Compared with phenylethyl alcohol, which is a bactericidal product employed both as an antiseptic and as a preservative, the products according to the invention have a higher average level of activity and are moreover soluble in water, which makes them much easier to use, particularly in galenical formulations.

The tolerance of the products according to the invention was studied on guinea-pigs. The animals are shaved on either side of the medial line of the back and shaving is repeated every 2 days. Groups of 6 receive 0.2 ml of an aqueous or alcoholic solution of the product according to the invention on the shaved area. If the products are in alcoholic solution, a control group of animals receives alcohol on one side.

To study the preliminary skin tolerance, the treatment is applied once a day, 6 days out of 7, for 3 weeks. The observations on the skin concern the presence of erythema, skin eruption or hyperkeratosis, the intensity of which is graded according to a fixed scale.

The skin sensitization test is carried out on the same animals after two weeks of rest. The treatment lasts one week and is identical to the previous treatment. The evaluation is made according to the same criteria and the same scale as those used for the local tolerance.

The products according to the invention were also investigated to determine whether they had a phototoxic or photoallergic effect on guinea-pigs. The technique used is that of J. UNKOVIC, G. MAZUE and J. GIRARD, Sciences et Techniques de l'Animal de laboratoire, volume 8 (3), 149–160 (1983). This is an adaptation of the techniques described by L. C. HARBER et al., Arch. Dermatol., 1967, volume 96, pp 646–656, and L. J. VINSON et al., J. Soc. Cosm. Chem., 1966, volume 17, pp 123–130.

None of the products studied showed poor tolerance, a sensitizing effect or a phototoxic or photoallergic effect on guinea-pigs.

The products according to the invention, which have a good antimicrobial activity and are well tolerated, can be used in a number of ways as antiseptics, preservatives or disinfectants for human purposes, in cosmetics and therapy, or veterinary purposes or in the food crop sector.

In particular, they can be used as antiseptics in preparations intended for therapy, for example in the treatment of impetigo, acne, infected forms of dermatosis, infected open wounds, closed infections such as furuncles, felon, impetiginous scabies, etc. It is also possible to envisage their use for preventive purposes, for example for the preparation of the surgical area or the preparation of the surgeon's or attendants' hands.

The products according to the invention can be used for veterinary purposes either as antiseptics (for example in the prevention of mammitis) or as disinfectants (disinfection of the equipment, the stalls or stables, etc.), and also in the food crop sector.

Finally, their good tolerance and low toxicity enable them to be used as preservatives not only in the fields of pharmacy and cosmetology but also in the food crop sector.

Different galenical formulations of the products according to the invention can be prepared according to the chosen use.

EXAMPLE 5

Foaming, detergent, antiseptic liquid preparation:

| | |
|---|---|
| SR 41613 A | 3 g |
| Alkyldimethylcarboxymethylamine (30% solution) | 15 g |
| Disodium tetracemate | 0.1 g |
| Propylene glycol | 10 g |
| Sodium hydroxide or lactic acid q.s. pH 5.8 | |
| Purified water q.s. | 100 g |

EXAMPLE 6

Foaming, detergent, antiseptic liquid preparation:

| | |
|---|---|
| SR 41946 A | 2 g |
| Sodium paraffinsulfonate | 15 g |
| Sodium hydroxide or lactic acid q.s. pH 5.2 | |
| Purified water q.s. | 100 g |

EXAMPLE 7

Disinfectant for an inert surface:

| | |
|---|---|
| SR 41579 A | 5 g |
| Dodecyldimethylcarboxydimethylamine | 20 g |
| Disodium tetracemate | 2 g |
| Lactic acid q.s. pH 3.5 | |
| Purified water q.s. | 100 g |

EXAMPLE 8

Antiseptic alcoholic solution:

| | |
|---|---|
| SR 41946 A | 2 g |
| Alkyldimethylcarboxymethylamine (30% solution) | 0.5 g |
| Ethylene oxide/propylene glycol condensate L 62 | 1 g |
| Sodium hydroxide q.s. pH 6.5 | |
| 70° ethyl alcohol q.s. | 100 g |

EXAMPLE 9

A product according to the invention can be used as a preservative in a shampoo:

| | |
|---|---|
| Palmitate of potassium and of aminoacids | 20 g |
| Sodium alkyl-sulfates | 2 g |
| Copra diethanolamide | 5 g |
| Linolyl acetate | 0.200 g |
| SR 41946 A | 0.150 g |
| Sodium hydroxide q.s. pH 7 | |
| Purified water q.s. | 100 g |

EXAMPLE 10

A product according to the invention can be used as a preservative in an emulsion cream:

| | |
|---|---|
| Thick vaseline oil | 6 g |
| Mixture of cetostearyl alcohol and methoxylated cetostearyl alcohol | 9 g |
| Anhydrous monosodium phosphate | 0.300 g |

| | |
|---|---|
| Disodium tetracemate | 0.010 g |
| Vaseline | 15 g |
| SR 41946 A | 0.150 g |
| Phosphonic acid q.s. pH 4.5 | |
| Purified water q.s. | 100 g |

EXAMPLE 11

A product according to the invention can be used as a preservative in a cream for cosmetological use:

| | |
|---|---|
| Collagen | 0.500 g |
| Carboxypolymethylene 934 | 0.400 g |
| Hydrogenated lanoline | 4 g |
| Perhydrosqualene | 20 g |
| Polymethoxylated sorbitol monopalmitate | 2 g |
| SR 41946 A | 0.150 g |
| Lactic acid or sodium hydroxide q.s. pH 6.5 | |
| Purified water q.s. | 100 g |

What is claimed is:

1. A benzamidine compound having a formula

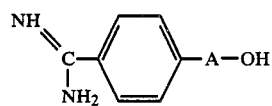

wherein: A is a linear or branched alkyl chain containing from 3-9 carbon atoms; and pharmaceutically acceptable salts thereof.

2. A benzamidine compound having a formula

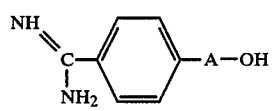

wherein: A—OH is —(CH$_2$)$_3$OH; —(CH$_2$)CHOH—CH$_2$—CH$_3$; —C(C$_3$H$_7$)$_2$CH$_2$OH; —(CH$_2$)$_4$OH; —(CH$_2$)$_5$OH; CH$_2$—CH(OH)n—C$_3$H$_7$ or —C(CH$_3$)$_2$CH$_2$OH; and pharmaceutically acceptable salts thereof.

3. A compound as claimed in claim 2, wherein A—OH is (CH$_2$)$_4$OH.

4. A compound as claimed in claim 2, wherein A—OH is (CH$_2$)$_5$OH.

5. A compound as claimed in claim 2, wherein A—OH is CH$_2$—CH(OH)nC$_3$H$_7$.

6. A compound as claimed in claim 2, wherein A—OH is C(CH$_3$)$_2$CH$_2$OH.

* * * * *